United States Patent [19]

Nakamura et al.

[11] Patent Number: 5,561,116
[45] Date of Patent: Oct. 1, 1996

[54] SOLID PRODUCT CONTAINING PROPOLIS COMPONENTS, AND PREPARATION AND USES THEREOF

[75] Inventors: Satoshi Nakamura; Toshio Miyake, both of Okayama, Japan

[73] Assignee: Kabushiki Kaisha Hayashibara Seibutsu Kagaku Kenkyujo, Okayama, Japan

[21] Appl. No.: 225,726

[22] Filed: Apr. 11, 1994

Related U.S. Application Data

[63] Continuation-in-part of Ser. No. 866,762, Apr. 10, 1992, abandoned.

[30] Foreign Application Priority Data

Apr. 11, 1991 [JP] Japan ................... 3-166538

[51] Int. Cl.$^6$ ............... A61K 31/70; A61K 31/715; C07H 1/00; C08B 37/16
[52] U.S. Cl. ................ 514/23; 514/53; 514/54; 514/58; 536/103; 536/124
[58] Field of Search ................ 514/58, 54, 53, 514/23; 536/124, 103

[56] References Cited

U.S. PATENT DOCUMENTS

| | | | |
|---|---|---|---|
| 4,382,886 | 5/1983 | Sosnowski | 530/200 |
| 4,702,915 | 10/1989 | Keri et al. | 424/195.1 |
| 4,810,827 | 3/1989 | Mitsuhashi et al. | 514/53 |
| 4,812,444 | 3/1989 | Mitsuhashi et al. | 514/53 |
| 4,816,445 | 3/1989 | Mitsuhashi et al. | 514/53 |
| 4,826,825 | 5/1989 | Mitsuhashi et al. | 514/53 |
| 4,870,059 | 9/1989 | Mitsuhashi et al. | 514/53 |
| 4,871,396 | 10/1989 | Tsujita et al. | 424/49 |

FOREIGN PATENT DOCUMENTS

| | | |
|---|---|---|
| 61-35800 | 2/1986 | Japan . |
| 197523 | 9/1986 | Japan . |
| 136240 | 6/1987 | Japan . |
| 152535 | 7/1987 | Japan . |
| 152536 | 7/1987 | Japan . |
| 152537 | 7/1987 | Japan . |
| 245159 | 9/1990 | Japan . |

OTHER PUBLICATIONS

J. F. O'Quinn, "Urine Therapy" published 1980 by Life Science Institute, pp. 1–36.

Shin–yaku Kaihatsu no tameno Dobutsu Model Riyo Shusei, edited by Ryuta Iteo et al., pp. 247–254, 1985 pub. by R & D Planing, Tokyo Japan.

Fragrance Journal 83, Magazine of Research and Development of raw materials for cosmetics, toiletries & allied industries; ISSN 0288–9803 Coden: Fjuad 7, 1987.

Natural Therapeutics, "Propolis", by Dr. Yves Donadieu; 2nd revision edition; translated by A. G. Jutel (1983).

Dr. Beatrice Barnett & Margie Adelman, "The Miracles of Urine Therapy", published 1987, pp. 1–84.

Szente et al. Acta Pharm. Technol., 33 (4) 218–222 (1987).

*Primary Examiner*—John Kight
*Assistant Examiner*—Everett White
*Attorney, Agent, or Firm*—Browdy and Neimark

[57] ABSTRACT

A solid, water-dispersible composition containing propolis components. This composition is prepared by extracting intact or dewaxed propolis with an aqueous solution of a water-soluble organic solvent to obtain propolis components, and mixing said propolis components with at least one saccharide selected from anhydrous saccharides and cyclodextrins to dehydrate the propolis components. The composition is suitable for use as a health food product, a sublingual agent, an additive for urine therapy, and for prevention and treatment of disease as well as in the promotion of recovery of health from diseases.

15 Claims, No Drawings

SOLID PRODUCT CONTAINING PROPOLIS COMPONENTS, AND PREPARATION AND USES THEREOF

The present application is a continuation in part of Ser. No. 07/866,762, filed Apr. 10, 1992, and now abandoned, the entire contents of which are hereby incorporated by reference.

FIELD OF THE INVENTION

The present invention relates to a solid product containing propolis components which has a satisfactory dispersibility in water, and preparation and uses thereof. More particularly, the present invention relates to a process for preparing a solid product containing propolis components which are soluble in a readily water-soluble organic solvent. The process for preparing these components includes a step of incorporating an aqueous solution of propolis components, which are soluble in a readily water-soluble organic solvent, into one or more saccharides selected from the group of anhydrous saccharides and cyclodextrins to effect dehydration and solidification of the propolis components.

DESCRIPTION OF THE PRIOR ART

Propolis is a heterogeneous, unstable, pastelike material which has significant biological activity. Because of its biological activity, it is widely used in pharmaceutical and cosmetic preparations. Propolis, also known as "bee glue", is produced by honey bees from plant secretions that are collected from the buds, young branches, and petioles of tress such as poplar, birch and willow. Honey bees complete the preparation of propolis by adding wax and their own saliva to the plant exudates collected.

Propolis designates a mixture of gums, resins and balms of viscous consistency which are gathered on certain parts, generally buds and bark of plants such as trees by bees. The bees return the propolis to the hive, where it is modified and mixed with other substances, essentially their own wax and salivary secretions.

The major species of trees which are known to contribute to the production of propolis are coniferous: pine, fir, spruce, some poplars, alder, willow, horse chestnut, birch plum, ash and oak.

Propolis has been used since the time of the ancient Egyptians. It was later used later by the ancient Greeks, who named it. Aristotle, among others, mentions propolis in his "story of the Animals" and considers it to be a remedy against all skin ailments, wounds and infections.

During the first century B.C., the famous Latin scholar Varron mentioned it in his work, as did the poet Virgil. In the beginning of our millenary, the Roman Pliny and the Greek doctor Dioscorde disputed its origin.

In the second century Galen mentioned it in his tracts. Propolis was also known to the Incas, were it was used for febrile infections.

Propolis has been used in France since the eighteenth century, but propolis was found to be particularly useful during the Boer War, about 1900, for disinfecting wounds.

Over the years, a number of very interesting properties have been attributed to propolis, among them:

(1) bacteriostatic and bactericidal properties which are effective on a number of bacteria, including some staphylococci, streptococci and salmonella, *Baccillus subtills*, alvei and larvae; *Proteus vulgaris; Escherichia coli B*. These antibacterial properties differ on whether the propolis is used in vitro or in vivo. The bactericidal effect is directly proportional to the concentration of the propolis.

(2) Fungicidal properties on some yeasts such as *Candida*, particularly *Candida albicans*, which can be responsible for creating mycosis or parasital ailments.

(3) Very powerful anesthetic properties, three to four times more powerful than cocaine, which may be related to the volatile oils contained in propolis;

(4) Stimulating and regeneration of tissue.

"Intact" propolis, i.e., propolis which has not been dewaxed, has various consistencies, depending upon the temperature. Propolis is hard and brittle at 15° C., but becomes soft and pliable at 30° C. Above 30° C., propolis is sticky, and melts at about 60° C. When propolis is gently heated over boiling water, is separates into two distinct parts: a viscous part which sinks, and a liquid part, propolis wax, which floats on the surface.

The microscopic structure of propolis is now well known because of a very extensive study conducted by Colette Jeanson and Philippe Marchenay on a scanning electron microscope. They examined samples collected from all over France, and found that the same microstructure is always found. This is believed to be because the bees contribute to the structure of the propolis, so that the properties of the propolis are always the same, independent of the source.

Generally, intact propolis has been found by chromatographic analysis to include the following components:

50–55% resins and balms

25–35% wax

10% volatile or essential oils

5% pollen

5% organic and inorganic compounds.

Among the organic compounds found in intact propolis are benzoic acid, gallic acid, cafreic acid, cinnamic acid, ferulic acid, isoferulic acid, p-coumaric acid, vanillin, isovanillin, esculetin, scopoletin, and flavonoids, including flavones such as acacetin, chrysin (which is responsible for the yellow color of propolis and beeswax), pectolinarigenin, pniocembrin, tectochrysin; flavonols, such as galaga, izalpinine, kaempferol, quercetin, rhamnocitrin; flavonones such as s pinostropnine and sakuranetin; and flavonols such as pinobanksine. Among the minerals which are part of propolis are aluminum, barium, boron, chromium, cobalt, copper, iron, lead, manganese, molybdenum, nickel, pewter, selenium, silicon, silver, strontium, titanium, vanadium and zinc.

Propolis can be collected from beehives by raking and scraping the frames or the walls of the hive, or by placing a flexible plastic or stainless steel screen on the comb, which the bees hasten to fill with propolis. Although the amount collected from each hive may vary greatly, the structure of the propolis is virtually the same.

The high relative humidity, optimum temperature and abundant presence of nutrients in the hives should result in very rapid propagation of molds and bacteria without the presence of propolis. However, the antimicrobial potency of propolis keeps the growth of such microbes under control. The long history of the use of propolis in folk medicine has undoubtedly proved the usefulness of propolis extracts in the treatment of many microbial infections and other diseases. Many papers and reports call attention to is remarkable pharmacological activities, including antimicrobial, antiinflammatory, burn-healing and wound-healing properties (cf. Wells, *Am. Bee J.* 116, 512 (1976) and Lavie, *Bull. Techn.*

*Apic.* 7, 13 (1980). Additionally, Shimuth et al., in *Pharmazie* 41, 131 (1986) have found that several water soluble components of propolis were found to inhibit the restriction endonucleases and bacterial DNA-dependent RNA-polymerases.

The chemical composition of propolis extracts is far too complicated and heterogeneous to be easily described, cf. Ghisalberti et al., *J. Experientia* 34, 157 (1978); Vanhaelen et al., *J. Chromatog.* 187, 255 (1980) and Suchy et al., *Farm. Obz.* 50, 543 (1981). The major chemical substance groups found in propolis extracts include phenoloids: about 20 different compounds, including vanillin, salicylic acid, cinnamic acid derivatives, ferulic acid, etc.; flavonoids, about 25 identified substances, including pinostronin, pinocembrin, sakunaretin, etc.; and terpenoid-like substances, only a few of which have been identified, including xantorroeol, acetoxy betulenol, etc.

The very complicated chemical composition and the sticky, non-wettable lipophilic properties of propolis extracts cause difficulties in the preparation of standardized propolis formulations for pharmaceuticals and cosmetics.

As noted above, propolis occurs in the form of a mass or lump, and the main components thereof are hydrophobic or only minimally soluble in water. Because of this limited solubility of the active ingredients in water, it has historically been difficult to use propolis in its naturally occurring form. Propolis thus has been used as a propolis extract in liquid, or an alcoholic tincture of propolis, which is prepared by extracting intact propolis with a relatively high concentration of a readily water-soluble organic solvent such as ethanol.

In order to improve the above drawbacks, several proposals have been made. For example, Japanese Laid-open Patent No. 197,523/86 proposes a process for preparing a propolis extract by dewaxing a liquid propolis extract which has been prepared by extracting intact propolis with a readily water soluble organic solvent, crystallizing and solidifying the components in the extract which have an antibacterial activity using a water-soluble filler, adding to the resultant mixture an emulsifier and an antioxidant, and drying the resultant mixture. However, this patent does not disclose the use of a saccharide nor of a propolis product which has a satisfactory water dispersibility.

Japanese Laid-open No. 245,159/90 proposes a food composition of propolis comprising propolis components which are soluble in a monohydric alcohol, a medium containing OH-base which can form multiple hydrogen bonds, and a surfactant in the form of polyol and fatty acid ester, wherein the surfactant is present in the food composition in the range of 0.01=25 parts by weight when the total amount of the propolis components and the medium is 100 parts by weight.

A number of ways of obtaining propolis components are known in the art. For example Japanese Laid-open No. 145,1159/90, provides the following methods for obtaining propolis extracts.

a. To a four-necked flask, equipped with a stirrer, thermometer, funnel and evaporator, was added 95 parts by weight of glycerin as an OH-base carrier having multiple hydrogen bondings, and one part by weight of tetraglycerin monooleate as a surfactant of a polyol fatty acid ester. The resulting mixture was stirred in vacuo at 40° C. for 15 minutes to obtain a glycerin solution with a homogeneously dispersed tetraglycerin monooleate.

To the glycerin solution obtained above was added dropwise in vacuo 50 parts by weight of an ethanol solution containing 10 w/w % propolis of Brazil while stirring at 40° C. The resulting mixture was heated to a temperature of 80° C., and the evaporator was initiated.

Thereafter, the resulting mixture was evaporated at 80°–85° C. and 50–100 mm Hg for one hour to remove 45 parts by weight of ethanol, followed by recovering a propolis food composition in the form of a brown colored solution containing five parts by weight of propolis components soluble in ethanol, 95 parts by weight of glycerin, and one part by weight of tetraglycerin monooleate.

B. To a hermetically sealed container equipped with a stirrer and a thermometer was added 85 parts by weight of glycerine as an OH-base carrier containing multiple hydrogen bonds, and 10 parts by weight of water. To the mixture was added 1.5 parts by weight of water, and to the mixture was added 1.5 parts by weight of tetraglycerin monooleate as a surfactant of a polyol fatty acid ester. The resulting mixture was stirred in vacuo at 60° C. for 30 minutes to form a mixture of glycerin and water with a homogeneously dispersed tetraglycerin monooleate. To the mixture thus obtained was added 15 parts by weight of propolis pieces from Brazil, mixed by stirring at 60°–70° C. for two hours in order to repeatedly contact the propolis pieces with the mixture solution. Thus was obtained a propolis food composition in the form of a solution of propolis components which are soluble in a solution of glycerin and water, and propolis sediments which are insoluble in the solution.

The resultant solution was filtered in vacuo at 70° C. by passing the solution through a 200-mesh metal wire netting to remove the insoluble propolis sediments, followed by recovering a propolis food composition with a dark green- and brown-colored solution containing 5 parts by weight of propolis components which are soluble in a solution of glycerin and water, and 1.5 parts by weight of tetraglycerin monooleate.

Szente et al., in *Acta. Pharm. Techol.* 33 (4) 218–221 (1987) disclose that propolis extracts can be formulated with cyclodextrin wherein the majority of the biologically active propolis constituents are entrapped in the molecular cavities of beta-cyclodextrin. However, when the cyclodextrin is mixed with the extraction liquid, there is as much as 13.9% water. It is impossible to use this cyclodextrin for dehydrating the extract of propolis. There is no disclosure that this preparation is satisfactorily water dispersible.

Mitsuhashi et al., In U.S. Pat. No. 4,810,827, disclose using anhydrous aldohexose as a desiccant. However, there is no disclosure or suggestion of using this desiccant for dehydrating propolis components contained in a hydrophilic organic solvent.

Sosnowski, in U.S. Pat. No. 4,382,886, discloses a method for extracting propolis to obtain a dry propolis powder. Unfortunately, it has been found that this amount of ethanol is not sufficient to prepare a propolis product that is readily dispersible in water.

Unfortunately, these proposals improved the water dispersibility of the propolis components, but, the processes were complicated and the final products had an unsatisfactory taste inherent to the emulsifier and surfactants which were used in the processes.

As described in Japanese Laid-open Patent No. 245,159/ 90, the following drawbacks obtain when such propolis extract is used as a food product for health:

(a) When a propolis extract is diluted with water, propolis components which are soluble in a readily water-soluble organic solvent precipitate, coagulate, or solidify into a nonuniform lump or mass;

(b) When a propolis extract is ingested orally, a relatively high concentration of a readily water soluble organic solvent contained in the extract, as well as the components dissolved in the solvent, are strong stimulants for the oral mucosa. After ingestion, the propolis extract is first diluted with gastric juices, and then the components are, as in the case with contact with water as described above, nonuniformly precipitated to cause an unpleasant sensation, as with stickiness in the mouth;

(3) A person who is allergic to an organic solvent cannot use such a propolis extract as food product for health; and (4) A propolis extract is in the form of a liquid, which reduces its handelability and portability.

There has been a great demand to overcome the drawbacks and to establish a solid product containing propolis components which can be prepared without using any emulsifier or surfactant, to produce a solid product having a satisfactory water dispersibility, taste preference, handleability and portability.

SUMMARY OF THE INVENTION

It is an object of the present invention to overcome the above-noted drawbacks. More particularly, the present inventors studied a process for preparing propolis extracts without using any emulsifier or surfactant to convert the active ingredients of propolis, which active ingredients are hydrophobic or only minimally soluble in water but are soluble in a readily water-soluble organic solvent, into a solid product which has a satisfactory water dispersibility and taste.

As a result, the present inventors found that a solid product containing propolis components, prepared by incorporating propolis components which were soluble in a readily water soluble organic solvent in at least one saccharide selected from anhydrous saccharides and cyclodextrins, had a satisfactory water dispersibility and taste, and completely overcame the conventional drawbacks of propolis products.

DETAILED DESCRIPTION OF THE INVENTION

The present invention relates to a solid product containing propolis components which have a satisfactory water dispersibility, and preparation and uses thereof. This process comprises incorporating active ingredients of propolis in at least one saccharide selected from anhydrous saccharides ad cyclodextrins. It is essential that the saccharide used be anhydrous. Additionally, the organic solvent which is soluble in water must be used in at least a 30% concentration in water in order to extract the propolis components which are required and to make the solid products of the present invention which are readily dispersible in water.

The "propolis components" of the present invention mean those compounds contained in propolis which dissolve in an organic solvent which is readily soluble in water. These propolis components are the active ingredients of propolis which have heretofore been used in a more crude state. The source of the propolis is immaterial, as the active ingredients of propolis are present in varying concentrations, but are all those compounds which dissolve in an organic solvent which is readily soluble in water. In other words, the propolis components are defined by their solubility in an organic solvent which is readily soluble in water.

The anhydrous saccharides which can be used in the present invention are those which can be converted into a hydrous crystal in the presence of water while exerting a dehydrating activity. Examples of these anhydrous saccharides are anhydrous maltose, lactitol, glucose, galactose, pratinose, raffinose, erlose and melezitose, as disclosed in Japanese Laid-Open Nos. 136,240/88, 152,535/88, 152,536/88 and 152,537/88.

The saccharides used are in the form of anhydrous crystalline saccharides having the lowest possible level of moisture, preferably a moisture content of 3 w/w % or less. It is preferred to use a saccharide having a moisture content of 2 w/w % or less, and the most satisfactory saccharide is FINETOSE®, a crystalline α-maltose powder commercialized by Hayashibara Co., Ltd, Okayama, Japan, and disclosed in Japanese Laid-open 35,800/86.

The cyclodextrins which can be used in the present invention are α-, β-, and gamma-cyclodextrins. One or more of these cyclodextrins can be used in the present invention.

If necessary, a practical starch hydrolysate containing a cyclodextrin together with at least one saccharide such as maltooligosaccharides, dextrins and branched dextrins can suitably be used in the invention.

In preparing a solid product according to the present invention, a cyclodextrin powder or a partial starch hydrolysate containing a cyclodextrin with the lowest possible level of moisture, i.e., below about 3 w/w % and preferably below about 2 w/w %, can be used in the present invention.

The "propolis components which are soluble in a readily water-soluble organic solvent" as referred to in the present invention are those components contained in intact propolis and which are soluble in a readily water soluble organic solvent. The preparations thereof include a step of extracting intact propolis or a dewaxed propolis preparation which has been prepared by dewaxing intact propolis with a solvent such as ethyl ether and ethyl methyl ether with a readily water soluble organic solvent, for example acetone, acetic acid or lower alcohols such as methanol, ethanol, and propanol, preferably with a relatively high concentration of aqueous solutions of the organic solvents, i.e., at least 30 w/w %, either at ambient temperature or heating up to reflux.

If necessary, intact propolis can be boiled into a suspension containing the propolis components. Alternatively, the α-glycosyl flavonoids as described in the present inventors' Japanese specification filed Apr. 11, 1991, entitled "α-Glycosyl Flavonoids and Their Preparation and Uses" can be used as the propolis components.

The propolis components in the form of solution or suspension usually contain a satisfactory level of moisture required in the present preparation of a solid product. When the moisture level of the propolis component is insufficient, an adequate amount of water can be advantageously added thereto.

In preparing a solid product according to the present invention, "incorporating in a saccharide a solution containing propolis components which are soluble in a readily soluble organic solvent" means processes which can incorporate the solution in the saccharide to homogeneity by stirring or mixing. For a satisfactory example, a process including a step of incorporating an ethanol solution, which contains propolis components, in one or more saccharides selected from anhydrous saccharides and cyclodextrins can be used, in which the amount of the ethanol solution compared with that of the saccharide is usually in the range of about 0.1–50 w/w % on the dry solid basis (d.s.b.), more preferably, in the range of about 0.2–30 w/w %, d.s.b.

The amount of propolis components to be administered is too low when the amount of the ethanol solution containing propolis components contains less than 0.1 w/w % d.s.b., and it is difficult to disperse a solid product in water when the amount of propolis components is more than about 50 w/w % d.s.b.

In the case of incorporating in a saccharide an aqueous solution containing propolis components, the existence of a relatively low level of moisture in the aqueous solution, preferably at least 1 w/w % or more, but lower than 50 w/w %, facilitates formation of a homogeneous dispersion and incorporation of the propolis components in the saccharide and permits inclusion or absorption of of a relatively large amount of propolis components in the saccharide. Thus, the amount of propolis components in the resultant solid product is increased, and the water dispersibility is greatly improved.

In order to dehydrate an aqueous solution containing propolis components which are soluble in a readily water soluble organic solvent into a solid product by incorporating the aqueous solution in a saccharide, the component mixture in the aqueous solution is dehydrated by adding at least one saccharide selected from anhydrous saccharides and cyclodextrins.

To promote the dehydration step effectively, the resulting mixture may be future admixed with at least one saccharide selected from the group of anhydrous saccharides and cyclodextrins. If necessary, the resulting mixture can be dried by heating.

Since the effective components of propolis are readily volatilized, deteriorated or decomposed by severe treatments such as irradiation by ultraviolet radiation or heating at a relatively high temperature, it is recommended to use a process in which the dehydrating action of an anhydrous saccharide is used at ambient temperature. This retains the effective components as much as possible. If necessary, a readily water soluble organic solvent can be removed by evaporation under the conditions that the conditions do not damage the active ingredients.

For such purpose, at least one saccharide selected from the group consisting of anhydrous saccharides and cyclodextrins with the lowest possible level of moisture are advantageously used.

The solid products thus obtained are usually in the form of a powder.

If necessary, the solid products can be further subjected to a pulverization or a spheroidization step.

The solid product produced by the present invention is a solid product containing propolis components which has a satisfactory water dispersibility, taste, and handelability.

It was found that the solid product of the present invention was as efficacious as conventional propolis extracts without the concomitant disadvantages of the conventional propolis extracts discussed above. The solid product of the present invention can thus be advantageously used as a food product for health, as an antibacterial agent, as a therapeutic agent in the maintenance and improvement of health, and in the prevention and treatment of diseases such as viral diseases, bacterial diseases, traumatic diseases, immunopathies, rheumatisms, diabetes, diseases of the circulatory system, malignant tumors and nervous diseases, as well as in promotion of recovery to health from such diseases.

In use, the solid product of the present invention is administered orally at a dose of about 0.1–5 g/day per adult, based upon the weight of propolis components. The dosage may be in one or several administrations per day. If necessary, the solid product can be formed into an ointment for parenteral use.

It was also found that the present solid product could favorably be used as an agent for imparting flavor to foods and pharmaceuticals, as well as a deodorant and agent for urine therapy.

Urine therapy, also known as uropathy, is described in *Kiseki ga okoru Nyo-Rycho*, edited by Ryoich Nakao, published by Makino Publisher, Tokyo, Japan (1990). According to this book, it has been known that health can be maintained and improved, and that diseases can be prevented and treated, by daily drinking about 100–200 mL of urine. It has also been known that such effects will be expected in proportion to the intake of urine without causing any side effects.

The unpleasant smell and taste of urine, however, prevent most persons from trying urine therapy. Alternatively, the unpleasant smell and taste of urine make persons reluctant to drink urine directly.

It was found that the solid product of the present invention, when dissolved in fresh urine, readily dispersed or dissolved in the urine and imparted a propolis flavor to the urine, diminishing the unpleasant smell of urine while improving the taste of the urine and augmenting the urine therapy. Thus, the solid product of the present invention can advantageously be used as an agent for urine therapy. These objectives are attained by using about 0.1–5 g of the solid product of the present invention in 100 mL of fresh urine.

The solid product of the present invention can be advantageously formed into a shape such as a granule, short rod, or tablet for its final form. Alternatively, the solid product can be processed into an ointment in which the solid product is incorporated.

Then the solid product is used as a sublingual agent or for external application, it can be formed, for example, into a tablet, ointment, or cataplasm.

If necessary, the solid product of the present invention can be formulated with ingredients derived from animal and/or plant sources, such as royal jelly, cod liver oil, egg oil, oyster extract, turtle extract, "Mamuishi (pit viper) extract, ginseng extract, *Saururaceae* extract, *Ginkgoaceae* extract, extract of Japanese apricot, loquat leaf extract, field horsetail extract, *Spirulina* extract and chlorella extract. Additional ingredients which may be incorporated in the solid product include vitamins such as thiamine, riboflavin, vitamin $B_{17}$, L-ascorbic acid, α-glycosyl L-ascorbic acid, rutin, α-glycosyl rutin, carotenoids, ergosterol and tocopherol. Additionally, hormones may be included in the compositions, such as insulin, growth hormone, urogastrone, erythropoietin, calcitonin, prolactin and sex hormones such as androgen and estrogen. Additional ingredients include biologically active substances including cytokines such as interferon, lymphotoxin, tumor necrosis factor, macrophage migration inhibitory factor, colony stimulating factor, transfer factor and interleukin 2. If necessary, more than one of these additives can be incorporated in the present solid product.

The following Experiments will explain the physiological activity of the present solid product containing propolis components.

Experiment 1

Preparation of a solid product containing propolis component

To one part by weight of a dewaxed propolis extract having about 30 w/w % propolis components prepared in accordance with the method of Example 5 was added 2 parts by weight of an anhydrous crystalline maltose powder. The resulting mixture was ventilated and dried at 40° C. to produce a solid product in powder form containing propolis components. By using the solid product thus obtained, the actions and activities of the present solid product were studied.

Experiment 2

Inhibition of Viruses

The virus inhibiting effects of the present solid product were studied using the plaque reduction assay which identified a plaque-depressing dose-50% ($PDD_{50}$) in which FL cells were infected with either vesicular stomatitis virus (VSV) or herpes simplex virus type 1 (HSV-1) which had been treated with a solution containing propolis components.

A propolis solution containing 10 or 50 µg/mL of propolis components was prepared by dispersion with or dissolving in Hanks' solution (pH about 7.4) a solid product in powder containing propolis component prepared by the method of Experiment 1. As a viral solution, a solution containing the virus to be studied in a concentration of about $10^2$–$10^4$ plaque forming units (PFU) per mL. was prepared. Half mL. aliquots of the propolis solution and the virus solution were mixed, and FL cells were infected to form plaques with viruses which had been treated with a solution of the mixture of propolis extract at 37° C. for one hour, followed by counting the resultant plaques.

As a control, a viral solution free of propolis components was prepared, and FL cells were infected as above with the viral solution to form plaques, followed by counting the resulting plaques.

The viral inhibitory rate (%) was calculated by the following formula:

Viral inhibitory rate (%) =

$$\frac{(Control\ plaques^*) - (Plaques^*\ of\ propolis\ tgreatment)}{Control\ plaques^*}$$

*In the above formula "plaques" means the number of plaques.

The relationship between the concentration of propolis components (µg/mL) and the viral inhibitory rate (%) is summarized in Table 1.

TABLE 1

| Virus | Form | Propolis components Concentration (µg/ml) | | |
|---|---|---|---|---|
| | | 0 | 10 | 50 |
| VSV | Extract | 0 | 29.4 | 48.3 |
| | Solid | 0 | 29.3 | 48.7 |
| HSV-1 | Extract | 0 | 100 | 100 |
| | Solid | 0 | 100 | 100 |

As can readily be seen from the results shown in Table 1, it was found that the presence of propolis components in a viral solution exhibited a strong viral inhibition. The level of this viral inhibition increased with increasing concentration of propolis components.

It was thus demonstrated that the viral inhibitory effect of the solid product of the present invention depended upon the amount of propolis components therein, and that the effect was almost the same level as that of conventional propolis extracts.

Experiment 3

STRESS INHIBITION

Experiment 3-1 Stress on Rats

In accordance with the method described by Matsuo et al. in *Shin-yaku Kaihatsu no tameno Dobutsu Model Riyo Shusei*, edited by Ryuta Ito, Ryo Takahashi and Nishio Honda, pp. 247–254 (1985), published by R&D Planing, Rokyo, Japan, male rats of Wistar strain, 280–350 grams each, were restrained in a stress cage made of wire nets, and the whole body except for the head was soaked in 23° C. water to induce an acute ulcer.

Experiment 3-2

Aqueous solutions were administered to rats as a stress inhibiting agent. These solutions were prepared by dissolving in distilled water a solid product containing propolis components obtained by the method in Experiment 1 to give prescribed concentrations. As a control, other rats were given distilled water or an aqueous solution which had been prepared by dissolving an anhydrous crystalline maltose in distilled water to give the prescribed concentration.

Each rat in a group consisting of 8 rats was orally dosed with 3 mL aliquots of stress inhibiting agents at 10 minutes prior to initiating stress loading on the rats.

The relationships among rat groups, stress inhibiting agents, and doses is summarized in Table 2.

TABLE 2

| Group | Stress inhibitory agent | Dose (mg)/3 ml/rat | Rat (Head) |
|---|---|---|---|
| I | Distiled water | | 8 |
| II | Anhydrous crystalline maltose | 9.0 | 8 |
| III | Solid product containing propolis components | 0.3 | 8 |
| IV | Solid product containing propolis components | 0.9 | 8 |
| V | Solid product containing propolis components | 3.0 | 8 |
| VI | Solid product containing propolis components | 9.0 | 8 |

Experiment 3-3

Evaluation of Effects

After completion of loading the stress, the rats were then administered ether and anatomized to measure the length in mm of each erosion formed on the surface of the stomach mucosa, followed by summing up the lengths to give the ulcer index of each rat.

The results are summarized in Table 3

TABLE 3

| Group | Stress inhibitory agent | Dose (mg)/ 3 ml/rat | Ulcer-index (mm) |
|---|---|---|---|
| I | Distilled water | | 63 |
| II | Anhydrous crystalline maltose | 9.0 | 56 |
| III | Solid product containing propolis components | 0.3 | 38 |
| IV | Solid product containing propolis components | 0.9 | 38 |
| V | Solid product containing propolis components | 3.0 | 36 |

TABLE 3-continued

| Group | Stress inhibitory agent | Dose (mg)/ 3 ml/rat | Ulcer-index (mm) |
| --- | --- | --- | --- |
| VI | Solid product containing propolis components | 9.0 | 27 |

Note: "Ulcer Index" is a mean value of a group of 8 rats.

As can readily be seen from Table 3, the ulcer indices of the rats in the groups which had been administered a solid product containing propolis component were as follows: The ulcer indices in groups III to V, which had been administered the solid product at a dose in the rage of 0.3–3.0 mg per rat, were lowered to about 60% as compared with group I, the control group which was administered distilled water. The ulcer index in group VI, which had been administered a dose of 9.0 mg./rat, was lowered to about 40% of that of group I. This clearly demonstrated that the solid product of the present invention exerted a strong stress-inhibitory effect.

The following examples are the preferred embodiments of the present invention. However, the present invention is not limited by these examples.

EXAMPLE 1

Intact propolis was extracted by conventional extraction means using a high concentration of an aqueous ethanol solution to obtain a propolis extract having about 65 w/w % ethanol, about 20 w/w % moisture, and about 15 w/w % propolis components. Five parts by weight of the propolis extract thus obtained was admixed with 2 parts by weight of gamma-cyclodextrin and five parts by weight of an anhydrous crystalline maltose powder. The resulting mixture was first ventilated and then dried at 40° C. for one hour, and then mixed to homogeneity with 7 parts by weight of anhydrous crystalline maltose into a solid product in powder form. One gram aliquots of the solid product were injected into laminated aluminum bags and sealed.

The product as obtained has a satisfactory water dispersibility and taste, and can advantageously used as a health food product, an antibacterial agent, a therapeutic agent, a flavor-imparting agent, a deodorant, and an additive for urine therapy in the maintenance and promotion of health, and in the prevention and treatment of disease, as well as in the promotion of recovery of health from diseases.

When the solid product of the present invention is used as a health food product, it can be taken alone or used by dispersing or dissolving about 0.2–1 gram of the solid in about 200 mL of tea, milk or juice, prior to use.

When the product is used as an additive for urine therapy, it can be used by dispersing or dissolving about 0.5–2 grams of the solid product in about 10 mL of fresh urine prior to use.

EXAMPLE 2

Intact propolis was extracted by conventional extraction means using a high concentration of an aqueous ethanol solution to obtain a propolis extract having about 74 w/w % ethanol, about 8 w/w % moisture and about 18 w/w % propolis components. Five parts by weight of the propolis extract thus obtained was mixed with an adequate amount of lemon flavor to provide a lemony flavor to the product and 5 parts by weight of DEXY PEARL$^R$ SD-20, a partial starch hydrolysate containing α-, β-, and gamma-cyclodextrins, commercialized by Ensuiko Seito Kabushiiki Kaisha, Yokohama, Japan. The mixture was first ventilated and then dried at 40° C. for one hour, and then admixed to homogeneity with 0.02 parts by weight of "α-G Sweet", a stevioside sweetener commercialized by Toyo Sugar Refining Co., Ltd., Tokyo, Japan, 0.02 parts by weigh of citric acid and 15 parts by weight of anhydrous crystalline maltose powder. The resulting mixture was treated with a granulator to obtain a solid product in granular form. One hundred gram aliquots of the solid product so obtained were injected into containers and sealed.

As with the product in Example 1, the product of this example had a satisfactory taste and water dispersibility, and can be advantageously used as a health food product, an antibacterial agent, and an additive for urine therapy in the maintenance and promotion of health, as well as in the prevention and treatment of diseases and promotion of recovery of health from diseases.

EXAMPLE 3

A solid product in granular form was obtained as in Example 22 except that the anhydrous crystalline maltose powder in Example 2 was replaced with anhydrous crystalline lactitol powder. The product was injected into bottles and sealed.

As with the product of Example 1, the product had a satisfactory taste and water dispersibility. This product can advantageously be used as a health food product, as an antibacterial agent and agent for urine therapy in the maintenance and promotion of health, and in the prevention and treatment of disease, as well as in the promotion of recovery of health from diseases.

EXAMPLE 4

A solid product in granular form was prepared by the method of Example 2. This product was tabletted in a conventional manner in a tabletting machine to product tablets of about 800 mg each.

The product so obtained is suitable for use as a health food product, especially as a sublingual tablet because the product gradually releases propolis components in the mouth, and the propolis components are readily absorbed via the oral mucosa. The product is favorably used as a cachou because one can continuously luxuriate in a propolis flavor.

EXAMPLE 5

Intact propolis was extracted in a conventional manner with a high concentration of an aqueous methanol solution to obtain a propolis extract, which Was then evaporated, dried, dewaxed by solid-liquid separation using ethyl ether, and dissolved in a relatively high concentration of an aqueous ethanol solution to obtain a dewaxed propolis extract containing about 70 w/w % ethanol, about 10 w/w % moisture and about 20 w/w % propolis components. Five parts by weight of the dewaxed propolis extract thus obtained was admixed with an adequate amount of a herb flavor and five parts by weight or a partial starch hydrolysate containing α-, β- and gamma-cyclodextrins, and the mixture was ventilated and dried at 30° C. for two hours. The mixture was further admixed to homogeneity with 0.5 parts by weight of calcium L-ascorbate and 20 parts by weight of an anhydrous crystalline maltose powder to obtain a solid product in powder form. Two gram aliquots of the solid product were injected into containers and sealed.

As with the product of Example 12, this product has a satisfactory water dispersibility and taste, and can advantageously be used as a health food product, an antibacterial agent, an additive for urine therapy in the maintenance and promotion of health, and the prevention and treatment of diseases, as well as in the promotion of recovery of health from disease.

EXAMPLE 6

Intact propolis was dewaxed with ethyl ether and extracted with a high concentration of an aqueous ethanol solution to obtain a dewaxed propolis extract having about 74 w/w % ethanol, about 8 w/w % moisture, and about 18 w/w % propolis components. Five parts by weight of the dewaxed propolis extract thus obtained was admixed to homogeneity with one part by weight of a ginseng extract hydrate and 10 parts by weight of an anhydrous crystalline glucose powder, and the resulting mixture was allowed to stand at ambient temperature for three hours. This mixture was further admixed to homogeneity with five parts by weight of anhydrous crystalline glucose powder to obtain a solid product in powder form. One gram aliquots of this solid powder were injected into laminated aluminum bags and sealed.

As with the product of Example 1, the product produced hereby had a satisfactory water dispersibility and taste and can be advantageously used as a health food product, an antibacterial agent and additive for urine therapy in the maintenance and promotion of health, and the prevention and treatment of diseases, as well as in the promotion of recovery of health from diseases.

Effect of the Invention

As is evident from the above, the solid product according to the present invention is prepared by incorporating propolis components, the main components of propolis, which are hydrophobic or minimally soluble in water but which are soluble in an organic solvent which is soluble in water, in one or more saccharides selected from anhydrous saccharides and cyclodextrins. The solid product thus obtained has a satisfactory water dispersibility and taste, and can overcome the drawbacks of conventional propolis extracts in liquid and other propolis products in solid form in which emulsifiers or surfactants must be used to prepare the product.

The solid propolis products of the present invention can be used in the same manner as conventionally obtained propolis extracts, without the concomitant disadvantages of the conventional propolis extracts. That is, the solid propolis products of the present invention can be advantageously used as health food products, as antibacterial agents, as therapeutic agents in the maintenance and promotion of health and the prevention and treatment of disease, as well as in the promotion of recovery of health from diseases.

It has also been found that the solid product of the present invention can advantageously be used as a flavor-imparting agent, deodorant, sublingual agent and additive for urine therapy.

Comparative Example

A solid product containing propolis components was prepared according to the method of Example 1 above. One hundred gram aliquots of an intact propolis preparation commercialized by Sansho Co., Let., Tokyo, Japan, were extracted by conventional extraction means with 100 g of 10, 14, 20, 25, 30, 40, 50, 60, 70, 80 and 90 w/w % aqueous ethanol solution and 100 g of absolute ethanol to obtain propolis extracts, which were then adjusted to a moisture content of 20 w/w %. Five parts by weight of each of the resulting propolis extracts was added to 14 parts by weight of anhydrous crystalline maltose, commercialized by Hayashibara Biochemical Laboratories, Inc., Okayama, Japan, in order to effect dehydration and removal of ethanol in the propolis extract, followed by the formation of a solid product in powder form.

According to the method of Example 1 of U.S. Pat. No. 4,382,886, hereinafter "Sosnowski", solid products of propolis were prepared except that 100 g aliquots of an intact propolis specimen commercialized by Sansho Co., Ltd., Tokyo, Japan, were extracted with 100 grams of 10, 15, 20, 25, 30, 40, 50, 60, 70, 80 and 90 w/w % aqueous ethanol solutions and 100 grams of absolute ethanol.

The water dispersibilities of the solid products obtained by both methods were evaluated as follows:

Fifty mL aliquots of distilled water were placed into 10 mL beakers, to which the solid products were added gradually with stirring at ambient temperature. The water dispersibility of each solid product was evaluated as "satisfactory" when the solid product was completely dispersed in the distilled water within 30 seconds. The product was deemed to be "unsatisfactory" when the solid product did not disperse within the distilled water and formed sediments. The final content of propolis components, on a dry solid basis, in a solid product, added to 10 mL distilled water, was determined when the solid product did not disperse in 100 mL distilled water and formed sediments.

The tastes of the solid products were evaluated by a panel of testers. The smell and taste of each solid product were evaluated by 20 panels. When 15 or more panels deemed the taste and smell "satisfactory", the solid product was evaluated as being "Satisfactory". Otherwise, the product was considered to be unsatisfactory.

The results are shown in Table 4,

TABLE 4

| Concentration of ethanol aqueous solution for extraction | Propolis components in ethanol extract (w/w %, d.s.b) | | Water-dispersibility of solid-product | Taste preference of solid product | Final content of propolis component dispersed in 100 ml distiled water (w/w%) (mg, d.s.b) |
| --- | --- | --- | --- | --- | --- |
| 10 | 8.3 | control | satisfactory | satisfactory | 4,500 |
|  |  | reference | satisfactory | unsatisfactory | 450 |
| 15 | 9.0 | control | satisfactory | satisfactory | 2,600 |
|  |  | reference | satisfactory | unsatisifiable | 250 |

TABLE 4-continued

| Concentration of ethanol aqueous solution for extraction | Propolis components in ethanol extract (w/w %, d.s.b) | | Water-dispersibility of solid-product | Taste preference of solid product | Final content of propolis component dispersed in 100 ml distiled water (w/w%) (mg, d.s.b) |
|---|---|---|---|---|---|
| 20 | 10.3 | control | satisfactory | satisfactory | 2,000 |
|  |  | reference | unsatisfactory | unsatisfactory | 190 |
| 25 | 11.0 | control | satisfactory | satisfactory | 1,300 |
|  |  | reference | unsatisfactory | unsatisfactory | 135 |
| 30 | 13.5 | control | satisfactory | satisfactory | 850 |
|  |  | reference | unsatisfactory | unsatisfactory | 80 |
| 40 | 18.3 | control | satisfactory | satisfactory | 440 |
|  |  | reference | unsatisfactory | unsatisfactory | 40 |
| 50 | 31.0 | control | satisfactory | satisfactory | 19 |
|  |  | reference | unsatisfactory | unsatisfactory | 2 |
| 60 | 40.3 | control | satisfactory | satisfactory | 10 |
|  |  | reference | unsatisfactory | unsatisfactory | trace |
| 70 | 41.5 | control | satisfactory | satisfactory | 8 |
|  |  | reference | unsatisfactory | unsatisfactory | trace |
| 80 | 42.4 | control | satisfactory | satisfactory | 9 |
|  |  | reference | unsatisfactory | unsatisfactory | trace |
| 90 | 43.1 | control | satisfactory | satisfactory | 7 |
|  |  | reference | unsatisfactory | unsatisfactory | trace |
| 100 | 37.9 | control | satisfactory | satisfactory | 5 |
|  |  | reference | unsatisfactory | unsatisfactory | trace |

Note: In table, the symbol "d.s.b" means the abbreviation of "on a dry solid basis".

It can readily be seen from Table 4 that the solid product prepared according to the present invention has a satisfactory water dispersibility and taste. The advantageous features are attained by a relatively simple procedure, and the active ingredients of the propolis are retained in a stable state.

While there has been described what is at present believed to be the preferred embodiments of the invention, it will be understood that various modifications may be made thereto, and this application is intended to cover in the appended claims all such modifications as fall within the true spirit and scope of the invention.

What is claimed is:

1. A process for preparing a water-dispersible solid composition consisting essentially of at least one saccharide and propolis components which are contained in intact propolis and dewaxed propolis and which are soluble in an aqueous solution of an organic solvent, said process consisting essentially of:

(a) selecting a quantity of material selected from the group consisting of intact propolis and dewaxed propolis;

(b) extracting said quantity of material with an aqueous solution of an organic solvent selected from the group consisting of acetone, acetic acid and water-soluble alcohols, wherein the concentration of said organic solvent in said aqueous solution is at least about 30 w/w %, to form a first extract containing propolis components which are contained in said quantity of material and are soluble in said organic solvent;

(c) evaporating water from said first extract to a moisture content of from about 1 w/w % to about 50 w/w % to form a second extract;

(d) incorporating said second extract in at least one saccharide selected from the group consisting of anhydrous saccharides and cyclodextrin in order to dehydrate the second extract, wherein the amount of said extract is in the range of from about 0.1–50 w/w % of said saccharide, on a dry solid basis;

(e) drying said dehydrated second extract at ambient temperature; and (f) incorporating said dried extract in an effective amount of at least one saccharide selected from the group consisting of anhydrous saccharides and cyclodextrins to obtain a water-dispersible solid composition.

2. The process according to claim 1 wherein said anhydrous saccharide is an anhydrous crystalline saccharide.

3. The process according to claim 2 wherein said anhydrous crystalline saccharide is selected from the group consisting of anhydrous maltose, lactitol, glucose, galactose, paratinose, raffinose, erlose and melezitose.

4. The process according to claim 1 wherein said water-soluble alcohol is selected from the group consisting of methanol, ethanol, and propanol.

5. The process according to claim 1 wherein the moisture content of said saccharide is less than about 3 w/w %.

6. The process according to claim 1 wherein said composition is in the form of a powder, granule, or tablet.

7. The process according to claim 1 wherein said water-dispersible composition is incorporated in a carrier selected from the group consisting of foods, antibacterial preparations, compositions for sublingual administration, and urine.

8. A pharmaceutical composition comprising a composition consisting essentially of at least one saccharide and propolis components, said propolis components being compounds which are contained in intact propolis and dewaxed propolis and which are soluble in an aqueous solution of an organic solvent, said composition being prepared by:

(a) selecting a quantity of material selected from the group consisting of intact propolis and dewaxed propolis;

(b) extracting said quantity of material with an aqueous solution of an organic solvent selected from the group consisting of acetone, acetic acid and water-soluble alcohols, wherein the concentration of said organic solvent in said aqueous solution is at least 30 w/w % to form a first extract;

(c) evaporating water from said first extract to a moisture content of from about 1 w/w % to about 50 w/w % to form a second extract;

(d) dehydrating said second extract by adding to said second extract at least one compound selected from the group consisting of anhydrous saccharides and cyclodextrins, the amount of said second extract being from about 0.1 to about 50 w/w % of said saccharide on a dry solid basis;

(e) drying said dehydrated second extract at ambient temperature; and (f) adding the dried extract to an effective amount of at least one carrier selected from the group consisting of anhydrous saccharides and cyclodextrins to obtain a water-dispersible composition;

wherein the composition is in a carrier selected from the group consisting of food products, antibacterial agents, carrier for sublingual administration, and urine.

9. The pharmaceutical composition according to claim 8 wherein the amount of propolis components in said pharmaceutical composition ranges from about 0.01 to about 5 grams of propolis components.

10. The pharmaceutical composition according to claim 8 wherein said anhydrous saccharide is an anhydrous crystalline saccharide.

11. The pharmaceutical composition according to claim 10 wherein said anhydrous crystalline saccharide is selected from the group consisting of anhydrous maltose, lactitol, glucose, galactose, paratinose, raffinose, erlose and melezitose.

12. The pharmaceutical composition according to claim 8 wherein said water-soluble alcohol is selected from the group consisting of methanol, ethanol and propanol.

13. The pharmaceutical composition according to claim 8 wherein the moisture content of said saccharide is below about 3 w/w %.

14. The pharmaceutical composition according to claim 8 in the form of a powder, granule, or tablet.

15. The pharmaceutical composition according to claim 14 wherein the amount of propolis components in said pharmaceutical composition ranges from about 0.01 to about 5 grams of propolis components.

* * * * *